United States Patent [19]

Durliat et al.

[11] Patent Number: 5,538,867

[45] Date of Patent: Jul. 23, 1996

[54] PROCESS FOR THE ELECTROCHEMICAL REGENERATION OF PYRIDINE COFACTORS

[75] Inventors: Helene Durliat, Castanet; Maurice Comtat, Toulouse; Jean-Luis Seris, Jurancon, all of France

[73] Assignee: ELF Aquitaine, Courbevoie, France

[21] Appl. No.: 258,773

[22] Filed: Jun. 13, 1994

Related U.S. Application Data

[63] Continuation-in-part of Ser. No. 919,379, Jul. 29, 1992, abandoned, which is a continuation of Ser. No. 404,455, Sep. 8, 1989, abandoned.

[30] Foreign Application Priority Data

Sep. 13, 1988 [FR] France .................... 88 11933

[51] Int. Cl.⁶ .................... C12P 39/00; C12P 19/36; C12N 13/00
[52] U.S. Cl. .................... 435/90; 435/42; 435/173.1; 435/829
[58] Field of Search .................... 435/90, 42, 173.1, 435/173.2

[56] References Cited

U.S. PATENT DOCUMENTS

| 4,318,784 | 3/1982 | Higgins et al. | 204/73 R |
| 4,464,235 | 8/1984 | Simon et al. | 204/73 R |

OTHER PUBLICATIONS

Schneider et al, Eur. J. Bio Chem 142: 75–84 (1984).
Egerer et al., BBA 703: 149–157 (1982).
Bader et al., J. Biotechnol. 1: 95–109 (1984).
ATCC Catalogue of Bacteria and Phages p. 273 (1992).

*Primary Examiner*—Irene Marx
*Assistant Examiner*—S. Saucier
*Attorney, Agent, or Firm*—Oblon, Spivak, McClelland, Maier & Neustadt

[57] ABSTRACT

The present invention relates to a process for the electrochemical regeneration of pyridine cofactors.

The process of the invention is characterized by the use, in a reaction medium subjected to electrolysis, of a cytoplasmic hydrogenase enzyme.

19 Claims, 1 Drawing Sheet

PROCESS FOR THE ELECTROCHEMICAL REGENERATION OF PYRIDINE COFACTORS

This application is a Continuation-in-part application of U.S. Ser. No. 07/919,379 filed on Jul. 29, 1992, now abandoned which is a Continuation application of U.S. Ser. No. 07/404,455 filed on Sep. 8, 1989, now abandoned. The entire contents of U.S. Ser. No. 07/919,379 are hereby incorporated by reference.

BACKGROUND OF THE INVENTION

1. Field of the Invention

The invention relates to a process for the electrochemical regeneration of pyridine cofactors which are used in processes for the enzymatic synthesis of organic products.

2. Discussion of the Background

The study of the use of oxidation/reduction enzymes in organic synthesis is expanding rapidly. These enzymatic synthesis processes employ pyridine cofactors such as NADH (nicotinamide adenine dinucleotide) which are involved in the oxidation/reduction mechanism. However, extrapolation of the results obtained in the laboratory onto a larger scale necessitates regeneration of the pyridine cofactors, which are much too expensive to be used in stoichiometric amounts. It appears, moreover, that the absence of sufficiently efficient methods is preventing the development on an industrial scale of processes for preparing commercial products. For this reason, many studies are currently in progress aimed at finding the optimal conditions for regeneration of these cofactors. The regeneration may be carried out chemically, enzymatically or electrochemically. Analysis of the advantages and drawbacks of these various approaches shows that no general regeneration technique is completely satisfactory, and it is advisable to envisage, in each particular case, optimization of the overall direct reaction/regeneration system (Applied Biochemistry and Biotechnology, Vol. 14, 1987 pp. 147–197).

The methods of regeneration of NADH, that is to say reduction of the $NAD^+$ form resulting from processes of reduction of the substrate to be converted, are illustrated in FIG. 1, in which:

S denotes the substrate to be converted.

P denotes the synthesis product to be obtained.

$E_1$ $E_2$ denote the enzymes involved in the mechanism, A and B the substrates and by products involved in the regeneration.

The mechanism a illustrates a chemical regeneration; the molecule bringing about the regeneration reduces $NAD^+$ directly to NADH. Hydrogen, used under pressure, has been proposed as a reducing molecule (Biotechnology and Bioengineering, Vol. 7, No. 9, 1985, pp. 1277–1281), but its use gives rise to problems of implementation and safety.

The mechanism b illustrates an enzymatic regeneration with an enzyme which accepts several substrates: the same enzyme catalyses the synthesis and regeneration reactions.

The mechanism c illustrates a process for synthesis and regeneration each employing a different enzyme and substrate.

The mechanism d illustrates an electrochemical regeneration.

In the case of the reduction of $NAD^+$, enzymatic methods have given the best results. Among enzymatic systems used, the following substrate/enzyme systems may be mentioned: formate/formate dehydrogenase, glucose 6-phosphate/glucose-6-phosphate dehydrogenase, glucose/glucose dehydrogenase, ethanol/alcohol dehydrogenase, hydrogen/hydrogenase.

The use has been proposed (Biotechnology letters 1983, 5(7), 463–468) of enzymes such as *Alcaligenes eutrophus* hydrogenase for reducing $NAD^+$ to NADH with hydrogen. However, the stability of the bound enzyme was very low, in particular as a result of oxygen or various oxidizing agents, prohibiting the development of an efficient process which, moreover, in no instance envisages an implementation of the electrochemical type.

Electrochemical processes appear attractive, at least theoretically, since they make it possible to set the rate of regeneration very readily by the choice of electrode potential, and to avoid the use of the regeneration enzyme and reagent (FIG. 1). Moreover, they offer the possibility of a ready monitoring of the reaction by measuring the intensity of electrolysis during the process. However, the advantages are limited by the incompatibility of some reagents capable of reacting directly with the electrode brought to the reduction potential; poisoning of the electrode by adsorbable products and reactants and a lack of selectivity are other major drawbacks. The latter problem is particularly appreciable in relation to reduction, as a result o the formation by one-electron transfer of the free-radical intermediate NAD· which is capable of dimerizing rapidly. The radical appears on the electrodes irrespective of their nature.

Some efforts have been made to overcome this problem by modifying the surfaces by bound chemical mediators, as well as by the use of mediators in solution. These attempts have not yet enabled sufficient selectivity to be produce and, as a result, the direct or indirect electrochemical reduction of $NAD^+$ has not been developed.

The electrochemical reduction of $NAD^+$ has been envisaged most especially on a mercury electrode, on which there appears chiefly the dimer $(NAD)_2$, and NADH in a few special cases. The emphasis is placed most especially on the mechanistic aspect and on the adsorption phenomena.

On a bare platinum electrode, reduction of $NAD^+$ gives a mixture of NADH and $(NAD)_2$; it takes place in the region of potential where gaseous hydrogen is evolved. The reduction is strongly dependent on the surface state of the electrode.

It has also been proposed (Journal of Biotechnology, vol. 1, 1984, pp. 95–109) to use mediators such as methyl viologen, often in combination with whole cells or cell extracts. In the mechanism, the mediator acts as a relay link in the transfer of electrons between the electrode and $NAD^+$, and participates in a reaction catalyzed by the biosystem. It should be noted that the appearance of free-radical intermediates impairs the yield; in addition, the mediator/biosystem biocompatibility is reduced.

SUMMARY OF THE INVENTION

The object of the present invention is to remedy the above drawbacks by proposing a process for the electrochemical regeneration of the pyridine cofactor NADH in the presence of a hydrogenase enzyme, the regeneration reaction and the synthesis reaction being carried out in the same medium and the same apparatus.

The subject of the invention is a process for the electrochemical regeneration of pyridine cofactors which are used in enzymatic synthesis processes by reduction of $NAD^+$ to NADH, characterized in that it is carried out by electrolysis on an electrode in the presence of a cytoplasmic hydrogenase enzyme.

DETAILED DESCRIPTION OF THE PREFERRED EMBODIMENTS

Aerobic bacteria capable of oxidizing hydrogen generally contain a soluble hydrogenase known as cytoplasmic hydrogenase, which reduces $NAD^+$, and a hydrogenase strongly bound to the membrane, incapable of reducing $NAD^+$ but whose role is to provide electrons for the generation of energy in an electron transport chain.

In the process of the invention, the cytoplasmic hydrogenase extracted from a bacterium containing the latter will be used. By way of example of bacteria containing this type of enzyme, there may be mentioned *Nocardia opaca* (which does not contain a membrane hydrogenase), *Alcaligenes eutrophus, Pseudomonas ruhlandii* and *Pseudomonas saccharophilia,* these latter containing both types of enzymes. Suitable cytoplasmic hydrogenases can also be obtained from bacteria of the genera of *Rhodococcus*, especially bacteria of the genera of *Rhodococcus sp.* which were previously identified as *Nocardia opaca.* The cytoplasmic hydrogenase of *Alcaligenes eutrophus* (ATCC 17699) will preferably be used and the cytoplasmic hydrogenase from *Nocardia opaca* 1b (DSM427) or *Rhodococcus sp.* DSM 427 is most preferably used.

The cytoplasmic hydrogenase *Nocardia opaca* 1b and *Rhodococcus sp.* can be obtained by conventional means known to those of ordinary skill in the art, such as the method described by Schneider et al. *Eur. J. Biochem.* 138, 533–541 (1984).

The soluble hydrogenase of *Alcaligenes eutrophus* possesses redox centers containing 2 flavin mononucleotides, 2 4Fe-4S clusters and 2 Fe-2S clusters of apparent standard potentials (pH 7) equal to –0.445 and –0.325 V, respectively, and also nickel. It differs from the soluble hydrogenases of anaerobic bacteria by its high molecular weight, its complex structure and its relative tolerance with respect to oxygen.

These properties make this enzyme a special case in the hydrogenase field as a result of the complex mechanisms involved in its functioning, which enables it to be used in the biotechnology field for the regeneration of NADH.

It appears that this mechanism of functioning permits a direct electrode-enzyme (hydrogenase) electron transfer which is especially favorable to the reduction of $NAD^+$ without the creation of $NAD^-$ radicals, precursors of $(NAD)_2$.

The flavin of the hydrogenase probably plays an important part in this transfer by providing for the electron relay link between the electrode and the Fe-S clusters which are reduced, as shown by the changes in the spectra.

Figure 1A:
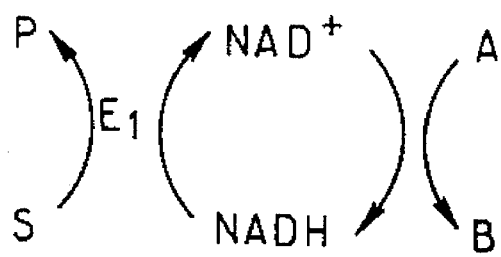
FIG. 1 provides an illustration of general methods for regeneration of NADH.
Figure 1B:
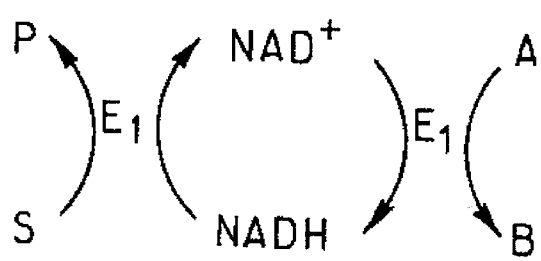
Figure 1C:
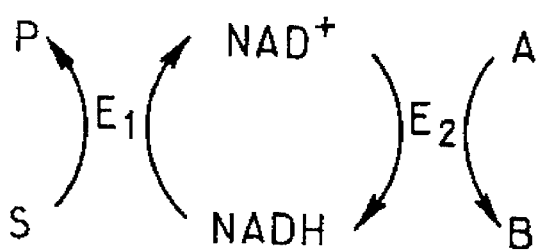
Figure 1D:
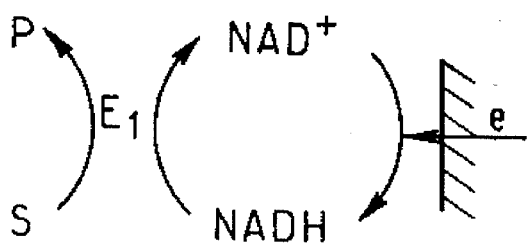
Figure 2:
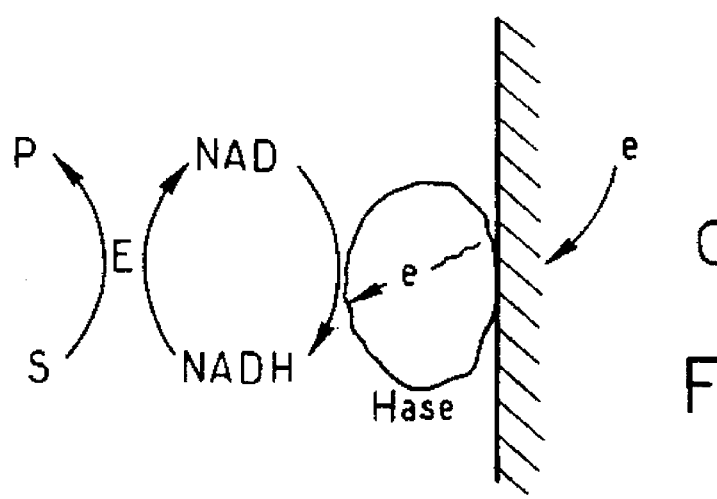
FIG. 2 provides a diagram of electrochemical regeneration using cytoplasmic hydrogenases.

The diagram of electrochemical regeneration using cytoplasmic hydrogenase is illustrated in FIG. 2, in which:

Hase denotes: *Alcaligenes eutrophus* hydrogenase

E denotes: the enzyme which catalyses the chemical reaction taking place in solution S and P denote: the substrate and product participating in the chemical reaction C denotes: the electrode, the cathode at which the electron is generated.

The electrochemical reduction of the enzyme may be detected by spectroscopy at a potential of –0.65 volt, reoxidation is initiated at –0.5 volt and completed at +0.1 volt.

Measurement of the enzymatic activity performed on the solution sampled after several reductions and reoxidations indicates that the electron transfer does not lead to a loss of activity. On the contrary, in the first few moments after electrolysis is stopped, a slight increase in this value is observed.

The enzyme hence plays a part of oxidation/reduction mediator between the electrode and $NAD^+$, and no denaturation of $NAD^+$ or NADH is seen when these molecules are placed in an electric field. Moreover, in contrast to direct reduction experiments, the dimer has never been detected. A facilitated two-electron transfer can probably be explained by the formation of the enzyme/$NAD^+$ complex in which the cofactor is in the most favorable structure for accepting two electrons, the enzyme acting as an electron relay link. Dimer formation does not take place, since the adsorption of $NAD^+$ or NAD on the electrode is probably prevented by a stronger adsorption of the enzyme.

In the process of the invention, any electrode incapable of being attacked, that is to say which remains in its original state in the presence of the solvent of the medium, containing or not containing oxygen and hence not being able to form with the said medium ions capable of passing into solution, may be used. By way of examples of usable electrodes, electrodes made of precious metals, gold, platinum, iridium (or alloys thereof), and carbon, tungsten or nickel electrodes, may be mentioned. Platinum electrodes will preferably be used.

The process of the present invention is preferably conducted in the absence of methyl viologen.

The process of the present invention is conducted ex vivo and therefor occurs outside of a biological or living cell.

The process of the present invention is conducted such that electrons are transferred directly from the electrode to the cytoplasmic hydrogenase.

The working conditions, temperature and pH, of the process of the invention are closely linked to the main synthesis reaction, providing for the latter the stability of the enzymes and a maximal yield. The temperature will generally be between 0° and 40° C. and the pH between 5 and 10.

The crucial point of the process is to set the electrolysis potential correctly. It will generally be between –0.5 and –0.9 volt, and preferably between –0.65 and –0.75 volt. It is important to avoid lowering this potential excessively, which would run the risk of leading to an evolution of hydrogen and hence a pH rise liable to denature the enzymes and/or substrate and to impair the rate of reaction.

The process of the invention is general in scope, that is to say it is usable for a wide range of enzymatic oxidation/reduction reactions. This versatility will be illustrated in the examples given below for several different reactions.

The precise working conditions for carrying out the process, namely potential, pH of the medium, composition are determined in each individual case, and by well known techniques, according to the direct enzymatic reaction to be carried out.

The bioelectrocatalytic regeneration of NADH is accomplished by reduction of $NAD^+$ in the presence of hydrogenase, coupled to an enzymatic reduction reaction according to the diagram in FIG. 2.

From a practical standpoint, a preliminary study must be carried out, consisting in verifying that, when the electrode is brought to the reduction potential of the hydrogenase and of NADH formation the substrate is not reduced directly the substrate and the product are stable the enzyme E does not lose its activity in the electric field.

Having generally described this invention, a further understanding can be obtained by reference to certain specific examples which are provided herein for purposes of illustration only and are not intended to be limiting unless otherwise specified.

The process of the invention is illustrated by Examples 1 to 3 below, relating to the regeneration of NADH used for carrying out the reactions 1 to 3.

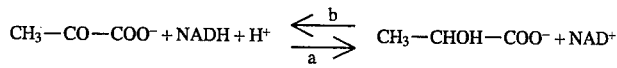

1

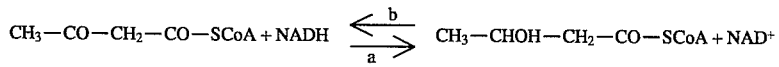

2

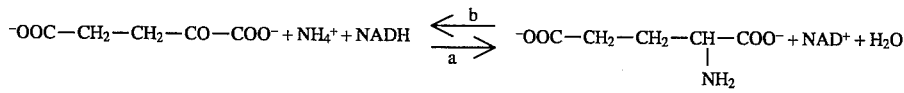

3

These reactions are catalyzed, respectively, by:

a rabbit muscle lactate dehydrogenase (LDH)

a porcine heart hydroxyacylcoenzyme A dehydrogenase (HyACoADH)

an ox liver glutamate dehydrogenase (GlDH)

For all these experiments, the thin-layer spectroelectrochemical technique was used. The electrolysis cell included a platinum electrode placed between two glass walls defining a volume of reaction medium of between 20 and 200 µl, similar to that used by De Angélis et al (J. Chem. Educ. 1976, 53,594). The measurements are performed by spectrophotometry (absorbance measurement).

These experiments on regeneration coupled to an enzymatic reaction consist of electrolyses at a potential determined previously in a conventional manner. The substrate, the cofactor and the two enzymes in solution in the medium appropriate to the reaction are introduced into the thin layer; after a reduction for 90 min, the solution is sampled and measurement of the concentrations of the product and the remaining cofactor is performed.

The electrolyte solutions are prepared from distilled water and from salts of high purity. The different solutions used are made in the following manner:

pH 6.5 and 7: solution of monopotassium and disodium phosphate 0.2M with respect to phosphate, or 0.05M solution of triethanolamine, HCl pH 8: 0.2M phosphate solution pH 9: 0.1M potassium carbonate solution or solution of glycine 0.6M, hydrazine 0.5M pH 10: 0.1M potassium carbonate solution The biological products are obtained from the company Sigma, with the exception of the cytoplasmic hydrogenase of *Alcaligenes eutrophus*, extracted according to conventional methods (Schneider K et al, Biochem. Biophys. Res. Commun 1978, 84, 564). The average concentration is 20 mg/ml with a specific activity equal to 40 U/mg. The other enzymes are of various origins: glutamate dehydrogenase is extracted from ox liver, hydroxyacetyl-CoA dehydrogenase from porcine heart and lactate dehydrogenase from rabbit muscle.

The different spectrophotometric assays are carried out employing the reactions stated above, and require only a few microliters of solution.

EXAMPLE 1 lactate and pyruvate: the reaction 1 and spectrophotometric assay of NADH at 340 nm are carried out. For lactate, the pH of the solution is equal to 9 in glycine medium, the reaction is relatively slow. The assay of pyruvate takes place in phosphate medium at pH 8, for which the reaction is rapid.

EXAMPLE 2 acetoacetyl-CoA: for assay of the reactant and of the product, the reaction 2, favored in the direction a at pH 7 and in the direction b at pH 10, is used; in both cases, the disappearance or appearance of NADH may be followed by spectrophotometry at a wavelength of 340 nm.

EXAMPLE 3

α-ketoglutarate: the assay is carried out in triethanolamine medium or in phosphate medium, the pH of the solution being equal to 7. 0.1M $NH_4^+$, 0.27 mM NADH and glutamate dehydrogenase are added, and the disappearance of NADH in the course of the reaction 3 is followed with the passage of time.

glutamate the solution has a pH equal to 8.6; the reaction 3 is used in the direction b, coupled to the reaction $NADH+INT+N^+ \rightarrow NAD^+ +formazan$, which favors displacement of the equilibrium 3 in the direction b(INT is iodonitrotetrazolium). The formazan is assayed spectrophotometrically at a wavelength of 492 nm.

The general conditions for these experiments and the results obtained are summarized in Table 1 below, relating to the regeneration of the cofactor by reduction of $NAD^+$.

| Ex. | Substrate to be reduced | NAD + mM | Hase | Enzyme E | Medium | Potential V | TTN |
|---|---|---|---|---|---|---|---|
| 1 | pyruvate 6 mM | 0.5 | 12 µL | LDH | phosphate pH 8 | −0.72 | 9 |
| 2 | acetoacetyl- | 0.5 | 20 µL | HyCoADH | phosphat | −0.68 | 6 |

-continued

| Ex. | Substrate to be reduced | NAD+ mM | Hase | Enzyme E | Medium | Potential V | TTN |
|---|---|---|---|---|---|---|---|
| 3 | SCoA 4 mM ketoglutarate 8 mM | 0.6 | 20 μL | 5 μL G1DH 1 mg/ml | e pH 7 TEA or phosphate + $NH_4^+$ pH 7 | −0.68 | 11 |
|   | then addition 9 mM | 0.4 | | | | | 12 |

TTN = ratio of the number of moles of product formed to the number of moles of cofactor in solution For these experiments, the electrolysis time was standardized at 90 min. The total turnover (TTN), that is the ratio of the number of moles of product formed to the number of moles of cofactor, was determined from the assessment of the concentrations of substrate and of product formed at the time of sampling, which enables it to be verified that the enzyme plays its normal part in the reaction under study. The results presented are the mean of 5 to 10 experiments for each substrate. They give rise to a few comments:

The TNN value is proof of the regeneration of the cofactor, and its low level arises only from the geometry of the cell and from the non-optimized experimental conditions for carrying out the regeneration.

$NAD^+$ reappears in toto in the native state at the end of the experiment, without detectable traces of dimer $(NAD)_2$. The process can be extended to other enzymatic reactions, and proves novel, since this appears to be the first example of the use of an enzyme as a direct electrochemical relay link between an electrode and $NAD^+$. Its implementation involves an optimization of the electrochemical reactor which, in particular, must be in an inert atmosphere. Furthermore, the accuracy of monitoring of the potential of the working electrode makes the electrochemical method a simpler and more selective tool than the reduction with molecular hydrogen which would use the same enzyme.

EXAMPLE 4

In order to demonstrate the influence of methyl viologen on the stability of NADH, the following experiment was conducted.

Sampled containing 0.5M phosphate solution at pH 8.0 and NADH at a concentration of $2 \times 10^{-3}$M, in variable concentrations of methyl viologen, were subjected to electrolysis at −0.70 V in relation to a reference electrode using standard calomel in a thin-layer cell with a useful volume of 30 to 40 μl for a period of 1 hour. The electrolyzed solution was then sampled and the quantity of NADH measured by means of the enzymatic reaction:

α ketoglutarate+$NH_4^+$+NADH→$NAD^+$+L-glutamate+$H_2O$ glutamate dehydrogenase The experimental conditions for dosage were as follows: a buffer medium of TEA 0.05M pH 7.3; α-ketoglutarate $5 \times 10^{-3}$M; $NH_4^+$ 0.2M; glutamate dehydrogenase 0.083 mg/ml.

The percentage of NADH that is lost was calculated in relation to the concentration of NADH measured in the same way from a control sample, which did not undergo electrolysis. In spite of the certain scattered results, the acceleration effect of methyl viologen on the degradation of NADH is clearly visible.

A process in which methyl viologen is not electrochemically reduced would provide for improved stability of NADH.

EXAMPLE 5

In order to demonstrate the improved rate of reduction of $NAD^+$ by the use of hydrogenase from Nocardia opaca, the following experiment was run.

A sample of hydrogenase from Nocardia opaca (DSM427) in a potassium phosphate buffer at 0.5M, pH 8.0 in a thin-layer cell of thickness of 0.03 cm, equipped with a platinum electrode and a standard calomel electrode as a reference containing 2 mM $NAD^+$, 0.1 mM of NADH and 10 unit/ml of hydrogenase was subjected to electrochemical potentials of −0.66 and −0.70 V/ECS. The rate of $NAD^+$ reduction was then measured. For the hydrogenase of Nocardia Opaca the rate of reduction was 0.6 mM/min at −0.66V and 1.5 mM/min at −0.70V.

In contrast, when the same experiment was conducted in the presence of hydrogenase from Alcaligenes eutrophus (ATCC 17699), the relative rates of reduction of $NAD^+$, was only 0.14 mM/min at −0.65V and 0.19 mM/min at −0.70V.

Thus, it was unexpectedly observed that the source of hydrogenase from Nocardia opaca gave an improved rate of reduction which is not suggested.

COMPARATIVE EXAMPLE 1

The Example 1 of the present invention (pyruvate; enzyme LDH; Potential: −720 mV) was repeated but without the addition in the medium of a cytoplasmic hydrogenase.

The result obtained was a TTN=0.

COMPARATIVE EXAMPLE 2

The Example 3 (ketoglutarate enzyme G1DH, Potential: −680 mV) was repeated but without the addition in the medium of a cytoplasmic hydrogenase.

The result obtained was a TTN=0.

The results obtained show that direct reduction of $NAD^+$ is practically impossible, especially with a reaction medium containing a lot of product. Such a reduction is theoretically possible, but needs very particular operating conditions (state of the electrode surface) and does not give a reduction rate and a reduction yield technically acceptable.

In the industrial processes, the cofactor is generally added to the medium in the oxidized form $NAD^+$. Then it is very advantageous to add to the medium (besides $NAD^+$) traces of NADH which allow to better initiate the reaction and to maintain this slight excess of NADH during the continuous process.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A process for enzymatically converting a substrate into a product comprising:
   a) electrochemically reducing a cytoplasmic hydrogenase enzyme obtained from *Rhodococcus sp.*, which were previously identified as *Nocardia opaca* DSM 427, with an electrode;
   b) transferring electrons from said cytoplasmic hydrogenase enzyme to a nicotinamide cofactor in the absence of methyl viologen;
   c) catalytically converting a substrate into a product with an enzyme and said nicotinamide cofactor; and
   d) regenerating said nicotinamide cofactor with said cytoplasmic hydrogenase.

2. The process of claim 1, wherein said electrode comprises a precious metal.

3. The process of claim 2, wherein said electrode comprises platinum.

4. The process of claim 1, wherein an electrolysis potential of between −0.5 to −0.9 volts is used.

5. The process of claim 1, wherein an electrolysis potential of between −0.65 to −0.75 volts is used.

6. The process of claim 2, wherein said process is conducted at a pH of between 5 to 10.

7. The process of claim 1, wherein an electrolysis potential of between −0.5 to −0.75 volts is used.

8. The process of claim 1, wherein NADH is added to the medium with the co-factor $NAD^+$.

9. The process of claim 1, wherein there is a direct electrode-cytoplasmic hydrogenase enzyme electron transfer.

10. A process for enzymatically converting a substrate into a product comprising:
    a) electrochemically reducing a cytoplasmic hydrogenase enzyme obtained from *Alcaligenes eutrophus* with an electrode;
    b) transferring electrons from said cytoplasmic hydrogenase enzyme to a nicotinamide cofactor in the absence of methyl viologen;
    c) catalytically converting a substrate into a product with an enzyme and said nicotinamide cofactor; and
    d) regenerating said nicotinamide cofactor with said cytoplasmic hydrogenase.

11. The process of claim 10, wherein said electrode comprises a precious metal.

12. The process of claim 11, wherein said electrode comprises platinum.

13. The process of claim 10, wherein an electrolysis potential of between −0.5 to −0.9 volts is used.

14. The process of claim 10, wherein an electrolysis potential of between −0.65 to −0.75 volts is used.

15. The process of claim 11, wherein said process is conducted at a pH of between 5 to 10.

16. The process of claim 10, wherein an electrolysis potential of between −0.5 to −0.75 volts is used.

17. The process of claim 10, wherein NADH is added to the medium with the co-factor $NAD^+$.

18. The process of claim 10, wherein there is a direct electrode-cytoplasmic hydrogenase enzyme electron transfer.

19. The process of claim 10 wherein said cytoplasmic hydrogenase enzyme is obtained from *Alcaligenes eutrophus* ATCC 17699.

* * * * *